United States Patent
Mohr et al.

(10) Patent No.: US 11,944,608 B2
(45) Date of Patent: Apr. 2, 2024

(54) TARGETING RNA VIRUSES USING INHIBITORS OF METTL3

(71) Applicant: New York University, New York, NY (US)

(72) Inventors: Ian Mohr, New York, NY (US); Hannah Burgess, Ridgewood, NY (US); Angus Wilson, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 17/511,044

(22) Filed: Oct. 26, 2021

(65) Prior Publication Data

US 2022/0125768 A1  Apr. 28, 2022

Related U.S. Application Data

(60) Provisional application No. 63/105,689, filed on Oct. 26, 2020.

(51) Int. Cl.
*A61K 31/437* (2006.01)
*C12N 15/113* (2010.01)

(52) U.S. Cl.
CPC .......... *A61K 31/437* (2013.01); *C12N 15/113* (2013.01); *C12N 2310/14* (2013.01); *C12N 2320/31* (2013.01)

(58) Field of Classification Search
None
See application file for complete search history.

(56) References Cited

FOREIGN PATENT DOCUMENTS

WO  WO2020/201773 A1 * 10/2020  .............. A61P 35/00

OTHER PUBLICATIONS

Zhang et al., bioRxiv (https://doi.org/10.1101/2020.10.14.338558, preprint posted Oct. 14, 2020), pp. 1-22.*

* cited by examiner

*Primary Examiner* — Brian J Davis
(74) *Attorney, Agent, or Firm* — Hodgson Russ LLP

(57) ABSTRACT

Provided are methods for prophylaxis or therapy for an RNA virus infection. The methods involve modulating the Type I interferon pathway in RNA virus infected cells of an individual. The Type I interferon pathway is modulated by administering one or more agents to virus infected cells that inhibit the expression and/or function of METTL3 or inhibit expression and/or function of YTHDF1, YTHDF2 or YTHDF3.

10 Claims, 9 Drawing Sheets

(9 of 9 Drawing Sheet(s) Filed in Color)

Specification includes a Sequence Listing.

hCoV-OC43 in MRC5
+ 3μM M3c or M3i and fixed @48 hpi

A.

siRNA treated MRC5 + hCoV-OC43

Dual detection of N immunofluorescence and DAPI by Cellinsight CX7scan

B.

C.

A.

B.

A.

B.

C.

D.

TARGETING RNA VIRUSES USING INHIBITORS OF METTL3

CROSS-REFERENCE TO RELATED APPLICATION

This application claims priority to U.S. provisional application No. 63/105,689, filed Oct. 26, 2020, the disclosure of which is incorporated herein by reference.

FIELD

The present disclosure relates to compositions and methods for prophylaxis and/or therapy of RNA virus infections using inhibitors of METTL3.

SEQUENCE LISTING

The instant application contains a Sequence Listing which has been submitted electronically in ASCII format and is hereby incorporated by reference in its entirety. Said ASCII copy, created Nov. 2, 2021, is titled "NYU_METTLE3_sequence_ST25.txt" and is 1,830 bytes in size.

BACKGROUND

A novel human coronavirus, SARS-CoV-2 (Zhou et al., 2020; Wu et al., 2020), alternately referred to as HCoV-19, that first emerged in Wuhan, Hubei province, China and causes an aggressive pneumonia (COVID-19) has rapidly spread and grown into a global pandemic (Li et al, 2020; Wang et al., 2020; Fauci et al., 2020). Infections and community-acquired transmission are now widespread world-wide and have resulted so far in greater than 243 million cases and over 4,900,000 fatalities (Johns Hopkins Univ. Coronavirus Resource Center). Within the USA, the outbreak has spread throughout the country and to date has resulted in greater than 45 million cases and over 737,000 fatalities. In the absence of a licensed vaccine and any FDA approved therapies, an urgent unmet medical need exists to rapidly investigate fundamental aspects of SARS-CoV-2 infection biology, as well as therapeutic targets and strategies for protection against, and treatment of, coronavirus infections. The present disclosure is pertinent to this need.

BRIEF SUMMARY

The present disclosure provides methods for prophylaxis or therapy for an RNA virus infection. In general, the method comprises modulating the Type I interferon pathway in RNA virus infected cells of an individual by administering one or more agents to the individual that inhibit the expression and/or function of METTL3 or inhibit expression and/or function of YTHDF1, YTHDF2 or YTHDF3. In non-limiting embodiments, the agents comprise an RNAi agent, a small drug molecule, or a combination thereof. The small drug molecule may have one of the following structures:

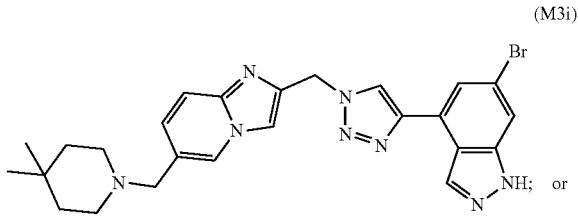

(M3i)

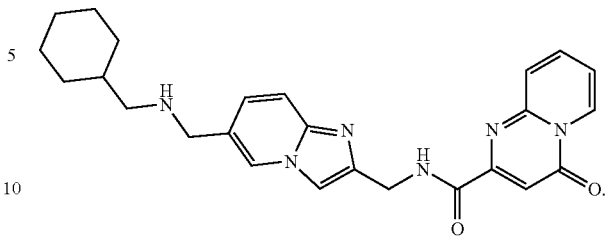

(M3i2)

The methods of the disclosure may be used against a variety of RNA viruses, non-limiting examples of which include any coronavirus, including but not necessarily limited to SARS-CoV-2, and variants thereof. The methods can be used for human and veterinary approaches.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
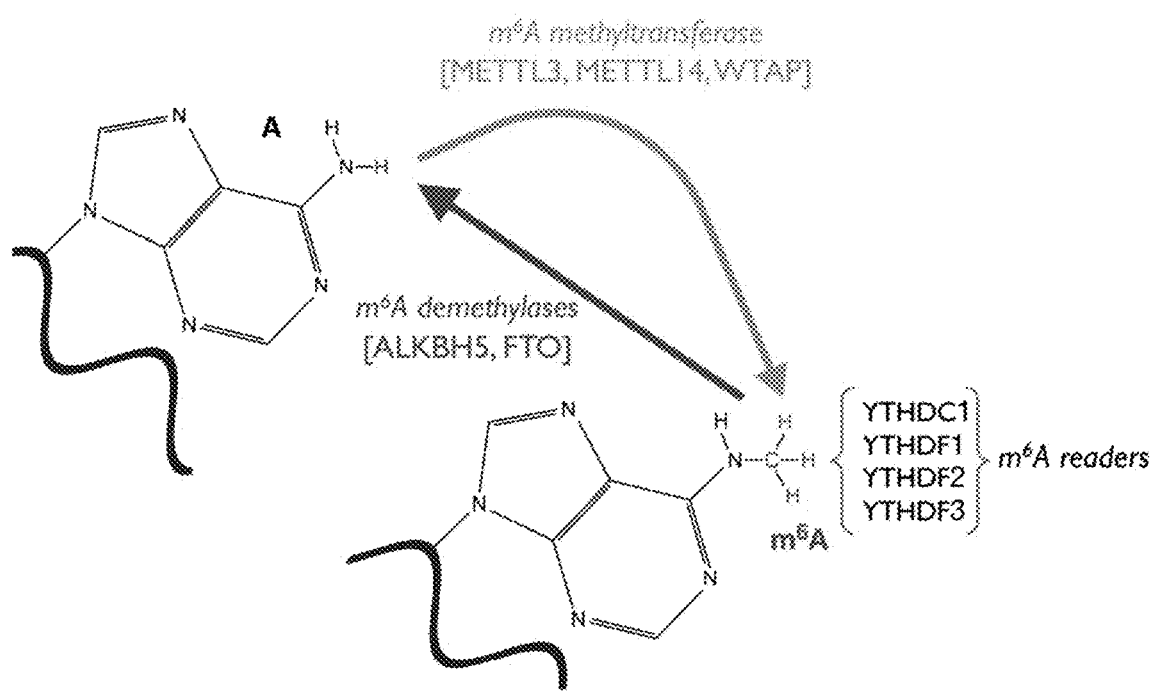
FIG. 1. Regulation of m$^6$A levels in mRNA. The opposing action of a multi-subunit methyltransferase and demethylases control m$^6$A RNA methylation. A subset of reader proteins that recognize m$^6$A-modified residues is depicted.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

Any sequence or compound associated with a database entry reference described herein is incorporated herein as it exists on the effective filing date of this application or patent.

The disclosure includes all polynucleotide and amino acid sequences described herein expressly and by reference, and every polynucleotide sequence referred to herein includes its complementary sequence, and its reverse complement. The disclosure includes all polynucleotide and protein sequences described herein expressly or by reference that are between 80.0% and 99.9% identical to the described sequences. Such changes can comprise conservative or non-conservative amino acid substitutions, insertions, and deletions, polymorphisms, and the like. Any one or combination of components can be omitted from the claims, including any polynucleotide sequence, any amino acid sequence, any composition of matter, and any one or combination of steps.

Data presented in this disclosure demonstrate that components of the cellular $m^6A$ pathway are important for coronavirus replication. Specifically, the data demonstrate that i) targeting METTL3 with a chemical inhibitor and RNAi-based approaches interferes with coronavirus replication; ii) inhibiting METTL3 activity, the primary host enzyme responsible for $m^6A$ installation onto RNA, and inhibiting one or more of YTHDF1, YTHDF2 or YTHDF3, reduces coronavirus replication; and ii) interfering with host $m^6A$ recognition functions reduces coronavirus gene expression and replication. Thus, the disclosure includes inhibiting the expression and/or function of METTL3 and/or the described YTHDF genes in cells infected with a coronavirus, which is expected to extend to any RNA virus. Accordingly, in embodiments and as described further below, the disclosure includes inhibiting the expression and/or function of METTL3 and/or the at least one of the described YTHDF proteins as an approach to prophylaxis and/or therapy of RNA viral infections. In embodiments, inhibiting the expression of METTL3 and/or the described YTHDF proteins is achieved using an RNA interference (RNAi)-mediated approach. In this regard, in non-limiting embodiments, RNAi-mediated silencing and/or reducing mRNA encoding METTL3 and/or mRNA encoding at least one of YTHDF1, YTHDF2 or YTHDF3 is performed. In embodiments, this is achieved by delivery of any suitable RNAi agent. In embodiments, an siRNA-based approach is used. This can be performed by introducing and/or expressing one or more suitable short hairpin RNAs (shRNA) in the cells, shRNA is an RNA molecule that contains a sense strand, antisense strand, and a short loop sequence between the sense and antisense fragments. shRNA is exported into the cytoplasm where it is processed by dicer into short interfering RNA (siRNA). siRNA are 21-23 nucleotide double-stranded RNA molecules that are recognized by the RNA-induced silencing complex (RISC). Once incorporated into RISC, siRNA facilitate cleavage and degradation of targeted mRNA. Thus, for use in RNAi mediated silencing or downregulation of METTL3 expression as described herein, siRNA, shRNA, or miRNA can be used. In alternative embodiments, a functional RNA, such as a ribozyme is used. In embodiments, the ribozyme comprises a hammerhead ribozyme, a hairpin ribozyme, or a Hepatitis Delta Virus ribozyme. In related embodiments, a microRNA (miRNA) adapted to target the relevant mRNA can be used. In embodiments, the RNAi agent may be modified to improve its efficacy, such as by being resistant to nuclease digestion. In embodiments, the RNAi agent polynucleotides which comprise modified ribonucleotides or deoxyribonucleotide, and thus include RNA/DNA hybrids. In non-limiting examples, modified ribonucleotides may comprise methylations and/or substitutions of the 2' position of the ribose moiety with an —O— alkyl group containing 1-6 saturated or unsaturated carbon atoms, or with an —O-aryl group having 3-6 carbon atoms, wherein such alkyl or aryl group may be unsubstituted or may be substituted, e.g., with halo, hydroxy, trifluoromethyl, cyano, nitro, acyl, acyloxy, alkoxy, carboxyl, carbalkoxyl, or amino groups; or with a hydroxy, an amino or a halo group. In embodiments modified nucleotides comprise methyl-cytidine and/or pseudo-uridine. The nucleotides may be linked by phosphodiester linkages or by a synthetic linkage, i.e., a linkage other than a phosphodiester linkage. Examples of inter-nucleoside linkages in the polynucleotide agents that can be used in the disclosure include, but are not limited to, phosphodiester, alkylphosphonate, phosphorothioate, phosphorodithioate, phosphate ester, alkylphosphonothioate, phosphoramidate, carbamate, carbonate, morpholino, phosphate triester, acetamidate, carboxymethyl ester, or combinations thereof.

In embodiments, and as described above, an agent that inhibits the expression and/or function of METTL3 may be used, and may be used alone or without compounds that inhibit the function of METTL3. Examples of such agents and approaches are described in PCT/US19/42784, published as WO 2020/023360, from which the description of METTL3, and inhibitors and inhibition of METTL3, is incorporated herein by reference. Representative and non-limiting embodiments of RNAi agents that target METTL3, as well as YTHDF1, YTHDF2 and YTHDF3 are described below.

In embodiments, the disclosure provides for inhibiting the function of METTL3 in RNA virus infected cells using one or more compounds, examples of which are described below. Combinations of RNAi agents and the described compounds are included in the approaches described herein. In embodiments, the compound is any small drug molecule that can inhibit the function of METTL3. A small drug molecule is generally a low molecular weight (e.g., less than 900 Daltons) organic compound that can affect the function of METTL3. The amino acid sequence and the DNA and RNA sequence encoding METTL3 are known in the art (NCBI Reference Sequence NM_019852.5).

In more detail, the present disclosure reveals a previously unexplored aspect of how coronavirus gene expression and replication are regulated post-transcriptionally. Significantly, both coronavirus gene expression (Huang et al., 2011; Lokugamage et al 2012, 2015) and anti-viral host responses (Rubio et al, 2018; Winkler et al, 2019) are both controlled by numerous post-transcriptionally regulatory mechanisms. In particular, it is known that RNA chemical modification can regulate virus gene expression, the reproduction of both DNA and RNA viruses and anti-viral host responses (Rubio et al, 2018; Winkler et al., 2019). However, how or if RNA chemical modification by $N^6$-adenosine methylation impacts reproduction of coronaviruses, including the recently emerged SARS-CoV-2 pandemic strain, is unknown and has not been previously described. Thus, without intending to be bound by any particular theory, it is considered that the present disclosure facilitates understanding how coronavirus gene expression is regulated by mRNA epitranscriptomic changes, and reveals new opportunities to interfere with coronavirus infection and provides new strategies for vaccine design and development and anti-viral drug discovery. In connection with this, differential chemical modification of mRNA imposes epitranscriptomic changes that dynamically alter gene expression. Among the numerous RNA chemical modifications, methylation of adenosine at the $N^6$ position ($m^6A$) constitutes the most widespread internal base modification to mRNA (Yue et al., 2015; Roundtree et al., 2017). RNA modification by $m^6A$ provides a powerful approach to influence developmental processes, disease pathogenesis, differentiation and reprogramming, circadian rhythm, cell cycle, and stress responses including virus infection (Fustin et al, 2013; Aguilo et al, 2015; Mer et al, 2015; Zhou et al, 2015; Wojtas et al, 2017; Vu et al, 2017; Wen et al, 2018) Virus-encoded mRNAs are also chemically modified by $m^6A$, and a role for $m^6A$ in infection biology is emerging (Williams et al, 2019). Moreover, it has been shown that host mRNAs, including those encoding powerful innate immune regulators like interferon beta (IFNB1) that orchestrate anti-viral responses, are also regulated by $m^6A$ modification and can regulate both RNA virus and DNA virus infection (Rubio et al, 2018; and PCT/US19/42784, published as WO 2020/023360). In this regard, epitranscriptomic $m^6A$ marks are installed on nascent mRNA cotranscriptionally by a methyltransferase writer core complex composed of the METTL3 catalytic subunit, METTL14, and WTAP (Liu et al., 2014) (FIG. 1). Distributed primarily within mRNA coding sequences and enriched at the start of 3'-exons and proximal to termination codons, $m^6A$ is also found within 3'-untranslated regions (UTRs) and extended 5'-cap structures where the 2'-O-methyl nucleotide adjacent to the 7-methylguanosine ($m^7G$) cap is an adenosine (Dominissini et al., 2012; Meyer et al., 2012). In addition to modifying RNA secondary structure (Roost et al., 2015; Liu et al, 2015; 2017), $m^6A$ is specifically recognized by a family of "reader" proteins, including YTH-domain containing proteins that reside mainly in the cytoplasm (YTHDF1, YTHDF2) or nucleus (YTHDC1, YTHDF3) (FIG. 1)(Patil et al., 2018). Identification of demethylases FTO and ALKBH5 that erase $m^6A$ marks in vitro suggested that $m^6A$ modifications were potentially dynamic and reversible, sculpted by the opposing actions of writers that install and erasers that remove $m^6A$ (Jia et al, 2011; Zheng et al, 2013). Recently, however, FTO was shown to have limited capacity to demethylate internal $m^6A$ residues with its preferred substrate being the $N^6$, 2'-O-dimethyl-adenosine ($m^6Am$) located adjacent to the $m^7G$ cap (Mauer et al, 2017). Although $m^6A$ methylation occurs to nascent pre-mRNA, it is largely stable in the cytoplasm until the mRNA decays (Ke et al, 2017; Rosa-Mercado et al, 2017). While this argues against methylation removal in the cytoplasm, both internal $m^6A$ removal by a demethylase like ALKBH5 within the nucleus or by newly synthesized cytoplasmic ALKBH5 protein could not be excluded and remain possible (Ke et al, 2017). Numerous aspects of RNA biology and metabolism are reportedly regulated by $m^6A$ mRNA modification including nuclear processing and export (Zheng et al, 2013; Fustin et al., 2013; Zheng et al, 2017; Haussman et al, 2016), translation (Meyer et al, 2015; Coots et al, 2017; Zhou et al, 2018) and mRNA decay (Wang et al, 2014; Du et al, 2016; Chen & Shyu, 2017; Edupuganti et al, 2017). These fundamental processes play critical roles regulating gene expression not only in uninfected cells, but in virus-infected cells as well. Without intending to be bound by any particular interpretation, it is considered that the present disclosure reveals for the first time the impact of host proteins that control RNA m$^6$A modification, including the catalytic methytransferase subunit METTL3, on coronavirus reproduction. In addition, how host m$^6$A modification enzymes gene expression in coronavirus-infected cells is described. Further, while m$^6$A has been detected in viral RNA, how host enzymes that control m$^6$A modification impact virus reproduction remains unclear and can vary. For two RNA viruses that replicate in the nucleus, cellular m$^6$A functions stimulate virus reproduction. The METTL3/14 m$^6$A writer complex reportedly promotes HIV replication whereas m$^6$A erasers ALKBH5 and FTO suppress it (Lichinchi et al, 2016a; Kennedy et al, 2016; Tirumuru et al, 2016). However, different mechanisms have been proposed to account for this including differential nuclear export, translation, and virus genome replication. Similarly, the METTL3 methyltransferase promotes influenza A virus replication and m$^6$A sites in the viral HA segment are required for proper protein expression and pathogenicity in mice (Courtney et al, 2017). Recently, RNA viruses that replicate exclusively in the cytoplasm have been found to contain m$^6$A in their (+) sense RNA genomes. Normally, cellular enzymes that install and remove m$^6$A are predominately found within the nucleus and the conditions that might alter their subcellular distribution to allow modification of non-nuclear RNAs produced by RNA viruses that replicate in the cytoplasm remain incompletely understood. In contrast with nuclear RNA viruses, m$^6$A writers METTL3/14 limited HCV infectious particle production and protein expression without detectably changing RNA replication (Gokhale et al, 2016; Gonzales-van Horn & Sarnow, 2017). The FTO demethylase, however, stimulated HCV protein expression. In addition, METTL3/14 restricted Zika virus reproduction whereas FTO and ALKBH5 demethylases enhanced it. Zika virus infection also enriched for m$^6$A modifications of host mRNAs but did not detectably change host anti-viral transcript abundance (Lichinchi et al, 2016b). Notwithstanding the above information, how cellular functions that control steady-state mRNA m$^6$A levels impact coronavirus gene expression and reproduction, including pandemic SARS-CoV-2, and host innate defenses like IFNB1, has been previously unknown, but is described in the present disclosure.

Thus, in certain embodiments, the present disclosure provides for a previously unexplored approach whereby reproduction of RNA viruses, including coronaviruses, further including but not necessarily limited to the pandemic SARS-CoV-2, is controlled epitranscriptomically by the host machinery that installs, removes and recognizes m$^6$A. Accordingly, in certain approaches, the disclosure provides for a method of modulating the type I interferon (IFN) pathway, such as by modulating interferon beta (IFNB1), in an individual in need thereof by administering to the individual one or more described agents that inhibits the expression and/or function of the METTL3. In embodiments, the administration results in increased IFN cytokine production and/or increased IFN mRNA in cells of the individual, to thereby provide an anti-viral effect. In embodiments, the disclosure provides a method of inhibiting the METTL3 methyltransferase in an individual to inhibit RNA virus replication, RNA virus gene expression, and/or packaging of viral RNA into a virion.

In embodiments, a composition comprising a one or more compounds described below is administered to an individual in need thereof. Compounds of this disclosure are as shown in the following structures:

referred to herein as M3i referred to herein as M3i2

The compound referred to as M3c is a control compound that has does not inhibit the function of METTL3. In embodiments, a composition comprising a compound of this disclosure is administered to an individual that has been diagnosed with, is suspected of having, or is susceptible to infection by an RNA virus. The described compounds and their uses include salts, partial salts, hydrates, stereoisomers, and mixtures thereof.

In embodiments, the individual may be infected with any virus that has an RNA genome. In embodiments, the RNA virus is a single or double stranded RNA virus. In embodiments, the RNA virus has a negative-sense, positive-sense, or ambisense RNA genome. In embodiments, the RNA virus has an intact single stranded genome, or a segmented RNA genome. In embodiments, the RNA virus is selected from Dengue Virus, Zika virus, Hepatitis C Virus, Hepatitis E virus, West Nile Virus, Ebola Virus, Rabies Virus, Polio Virus, Measles Virus, and any member of the virus family Coronaviridae, including but not necessarily limited to RNA viruses that cause any of severe acute respiratory syndrome (SARS), Middle East respiratory syndrome (HERS), coronavirus disease 19 (COVID-19) as caused by SARS-CoV-2, or feline Coronavirus (FCoV) that can lead to the development of feline infectious peritonitis (FIP).

In embodiments, the composition is administered to an individual who is at risk for contracting a SARS-CoV-2 infection, and thus may be administered prophylactically. In embodiments, a composition of the disclosure is administered to an individual who is infected with SARS-CoV-2, or is suspected of having a SARS-CoV-2 infection. In either case, the individual may be in need of prophylaxis or treatment of an infection caused by any SARS-CoV-2 variant, including but not necessarily limited to variants currently referred to as variants of interest, variants of concern, and variants of high consequence. In embodiments, the SARS-CoV-2 variants include a spike mutation that is an L452R or E484K spike protein amino acid substitution. In embodiments, the described variant is currently referred to as B.1.1.7, B.1.351, P.1, P.2., B.1.427, B.1.429, B.1.526.1, or B.1.617.2, the latter currently referred to as the delta variant.

In embodiments, a composition of this disclosure is administered to an individual who has been diagnosed with COVID-19. In embodiments, the individual is a human and is of an age wherein risk of developing and/or experiencing adverse outcomes due to having COVID-19 is heightened, such as any individual over the age of 50 years. In embodiments, the individual has an underlying condition wherein the risk of developing severe symptoms of a Coronavirus infection, such as COVID-19, is increased, including but not necessarily limited to any respiratory condition. In embodiments, the individual is a non-human mammal that is infected with a coronavirus, such as a feline mammal, but administering the compositions to any other non-human mammals that are infected, susceptible or may become susceptible to coronavirus infections are included in the disclosure.

In embodiments, an effective amount of a composition is administered to an individual. An effective amount means an amount of the described compound(s) that will elicit the biological or medical response by a subject that is being sought by a medical doctor or other clinician. In embodiments, an effective amount means an amount sufficient to prevent, or reduce by at least about 30 percent, or by at least 50 percent, or by at least 90 percent, any sign or symptom of viral infection. In embodiments, fever is prevented or is less severe than if the presently described compound(s) had not been administered to an infected individual. In embodiments, viral pneumonia is inhibited or prevented in an infected individual. In embodiments, transmission of the virus from an infected individual to a non-infected individual is inhibited or prevented. In embodiments, a compound of this disclosure is used in a concentration of at least 10 uM.

In embodiments, the described compound(s) are provided in the form of a pharmaceutical formulation. A pharmaceutical formulation can be prepared by mixing the compound(s) with any suitable pharmaceutical additive, buffer, and the like. Examples of pharmaceutically acceptable carriers, excipients and stabilizers can be found, for example, in Remington: The Science and Practice of Pharmacy (2005) 21st Edition, Philadelphia, PA Lippincott Williams & Wilkins, the disclosure of which is incorporated herein by reference.

Administration of pharmaceutical formulations comprising the described compound(s) of this disclosure can be performed using any suitable route of administration, including but not limited to parenteral, intraperitoneal, and oral administration. Parenteral infusions include intramuscular, intravenous, intraarterial, intraperitoneal, and subcutaneous administration. The compositions can be administered to humans, and as described above, are also suitable for use in a veterinary context. In embodiments, a single administration is administered and is sufficient for a therapeutic response. In embodiments, more than one administration is provided.

In embodiments, administration of the described compound(s) can be combined with any other suitable anti-viral therapy, including but not necessarily limited to passive immunotherapies, vaccinations, and anti-viral compounds, such as Remdesvir and Galidesivir.

In connection with the Examples below, it has been demonstrated that host anti-viral defenses are regulated by the host $m^6A$ machinery in response to DNA and RNA virus infections (Rubio et al, 2018) and (Winkler et al, 2019). In addition, the cellular $m^6A$ modification machinery can influence reproduction of RNA viruses that replicate in the nucleus (influenza, HIV) and cytoplasm (flaviviruses). However, as discussed above, how the cellular $m^6A$ modification machinery influences reproduction of coronaviruses, including the pandemic SARs-CoV-2, has been previously unknown. Accordingly, and without intending to be constrained by any particular theory, it is considered that the present disclosure establishes fundamental features of how the cellular $m^6A$ machinery responds to coronavirus infection, and how interfering with host $m^6A$ modification components impacts coronavirus reproduction. The Examples provide comparisons between the pandemic SARs-CoV-2 with a non-pandemic, related circulating human beta-coronavirus associated with predominately mild respiratory symptoms (hCoV-OC43) to evaluate if the results pertain in general to human coronaviruses or may to any extended to be specific to SARs-CoV-2 pandemic or non-pandemic (Carman et al., 2018) strains. This knowledge gap addressed in the Examples. In particular, to analyze the two described viruses in cell culture, different model cell systems were used to support the replication of these different viruses. SARS-CoV-2 infection biology was investigated using naturally permissive Calu-3 (epithelial origin, human lung adenocarcinoma) cells, while MRCS (limited lifespan normal human diploid lung) human fibroblasts were used to study hCoV-OC43.

The following Examples are intended to illustrate various embodiments of the disclosure, but are not intended to be limiting.

Example 1

Inhibiting METTL3 suppresses human coronavirus replication.

Figure 2:
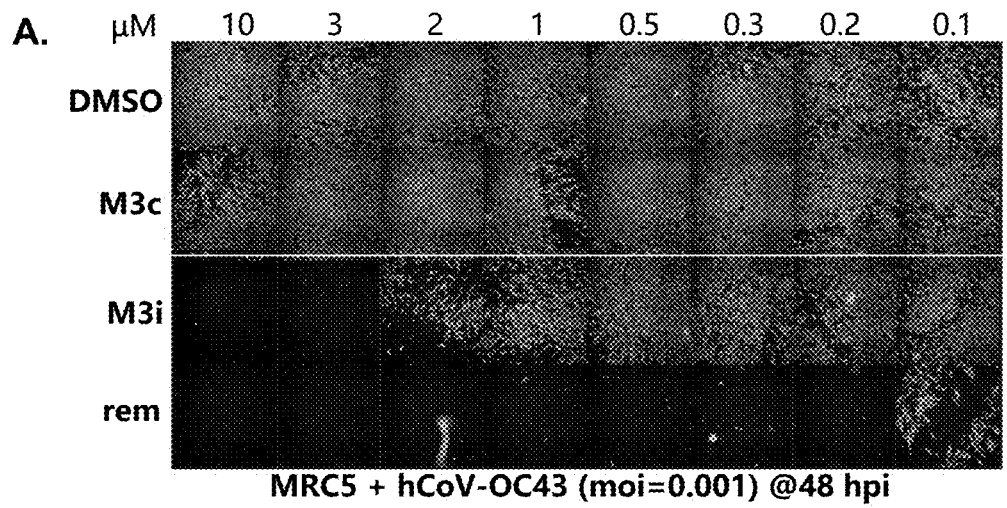
FIG. 2. Inhibiting METTL3 in lung fibroblasts suppresses hCOV-OC43 replication. (A) MRCS cells infected with hCOV-OC43 [MOI=0.001] were treated with vehicle (DMSO), control compound (M3c), active METTL3 inhibitor (M3i) or (+) control antiviral remdesivir (rem). Viral spread through the culture was determined by immunofluorescence using an antibody to the hCoV-OC43 nucleocapsid protein (green stain). (B) Quantitation of N protein positive cells from (A) (n=3; **P<0.005; *P<0.05 by t-test for M3c vs M3i). Suppression of viral replication by M3i is evident from >0.5 mM and higher. (C) Test compounds (3 mM) have no significant impact on MRCS viability (n=3) after 48 h of treatment.
Figure 2:
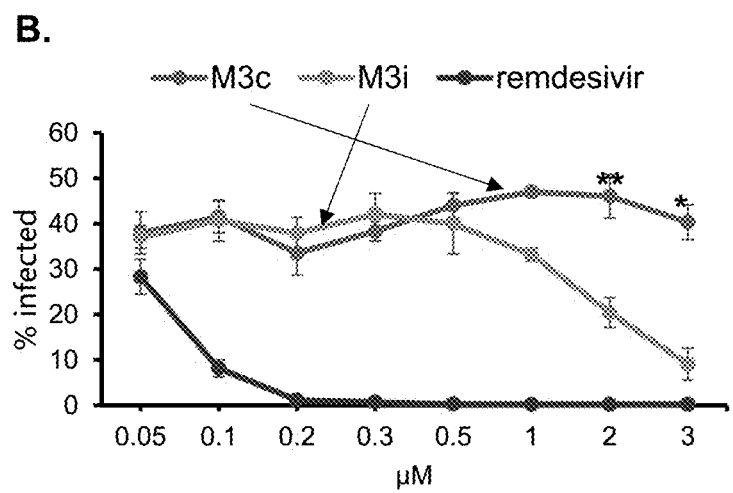
Figure 2:
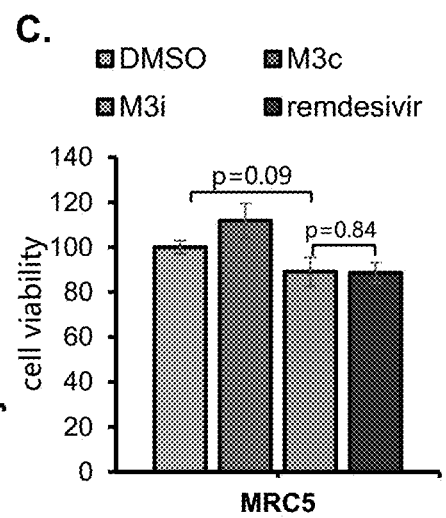
Figure 3:
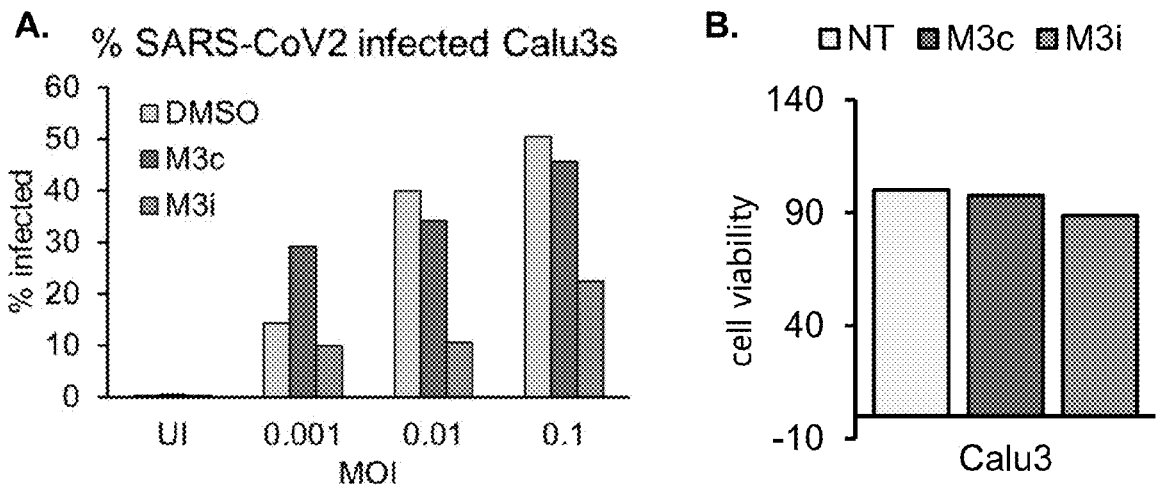
FIG. 3. Inhibiting METTL3 restricts SARS-CoV-2 replication in Calu-3 cells. (A) Calu-3 cells infected at the indicated MOI with SARS-CoV-2 were treated with vehicle (DMSO), control compound (M3c) or selective METTL3 inhibitor (M3i). Viral spread through the culture was determined by immunofluorescence using a commercial antibody to the SARS-CoV-2 Spike protein. (B) METTL3 inhibitor has minimal impact on viability of Calu-3 cell at concentrations of 3 mM or lower.
Figure 4:
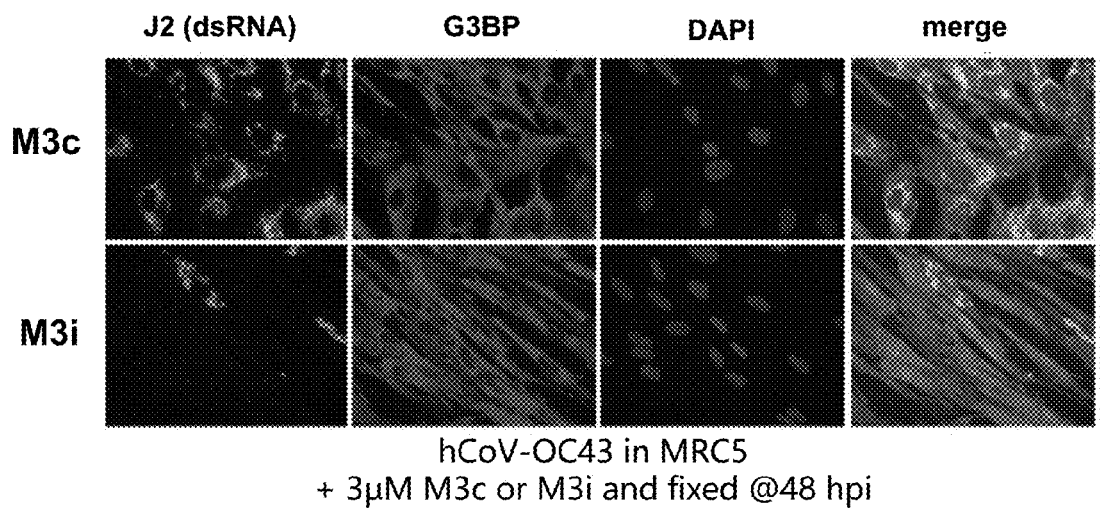
FIG. 4. M3i blocks viral dsRNA accumulation. J2 antibody detects dsRNA; no impact on stress granule marker G3BP staining was detected.
Figure 5:
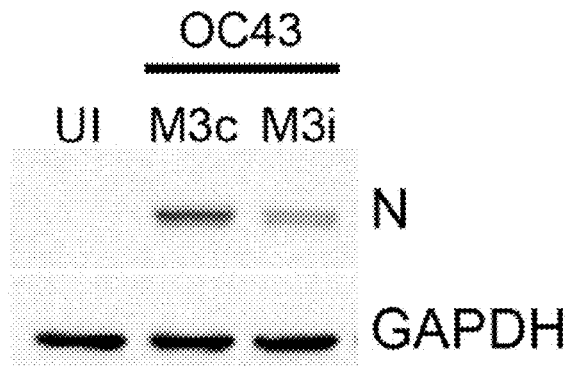
FIG. 5. Immunoblot showing reduced N accumulation in infected MRCS cells after 24h M3i treatment.

Inactivation of METTL3 in embryonic stem cells has been shown to abolish 99% of cellular $m^6A$ arguing that this is the principal enzyme (Geula et al., 2015). To evaluate how METTL3 enzymatic activity impacted coronavirus reproduction, we compared the activity of a specific METTL3 chemical inhibitor (Tzelepis et al., 2019), here termed M3i, to a structurally related control compound M3c unable to inhibit METTL3. M3i is highly selective for METTL3 and is being developed to treat acute myeloid leukemia (Tzelepis et al., 2019). To measure coronavirus replication, we developed an assay (FIG. 2A) that uses indirect immunofluorescence to detect coronavirus nucleocapsid protein (N) to monitor and quantify virus reproduction and spread using a high-content imaging platform (Cellinsight CX7 LZR). While both M3i and M3c had negligible detectable effects and appeared to be non-toxic on MRCS (FIG. 2C) or Calu-3 (FIG. 3B) cell viability over the dosage range tested, M3i strongly suppressed hCoV-OC43 replication and spread at 0.5 µM or higher (FIG. 2A,B). In FIG. 2C, the bars from left to right indicate DMSO, M3c, M3i, and remdesivir. SARS-CoV-2 replication in Calu-3 cells was also significantly reduced by M3i but not by M3c (FIG. 3A). In FIG. 3A, the bars from left to right represent DMSO, M3c and M3i. In FIG. 3B, the bars represent Not Treated, M3c and M3i. This reflects a significant reduction in the accumulation of viral RNA as measured by RT-qPCR (not shown), or immunofluorescence using dsRNA-specific antibody (FIG. 4) and is reflected in reduced N expression at 24 hpi (FIG. 5). These results indicate that active deposition of $m^6A$ by METTL3 is required for effective replication of both SARS-CoV-2 and hCoV-OC43, independent of cell type. It is believed this requirement will extend to other RNA viruses, including coronaviruses with pandemic potential. The data further provide proof in principle that the cellular m$^6$A modification machinery represents an unexpected host target for anti-coronavirus drug targeting.

Example 2

Figure 6:
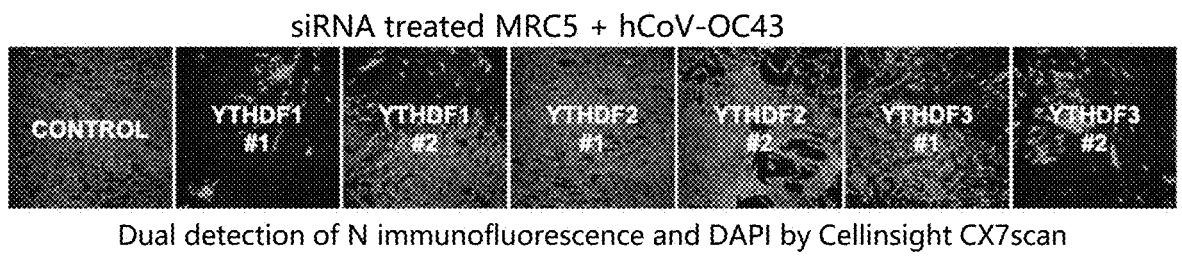
FIG. 6. Depletion of YTHDF readers suppresses hCoV-OC43 and SARS-CoV-2 replication. Cultures of MRCS (A, B) or Calu-3 (C) cells were seeded in multi-well plates and transfected with two validated siRNAs for each YTHDF reader protein or a non-silencing siRNA control two days prior to infection with either hCoV-OC43 or SARS-CoV-2, respectively. (A) Representative combined N protein immunofluorescence (green) and DAPI staining (blue) imaged using a high-throughput Cellinsight CX7 LZR plate scanner. (B & C) Image J quantitation showing percentage of cells that are virus-infected in each siRNA-treated culture.
Figure 6:
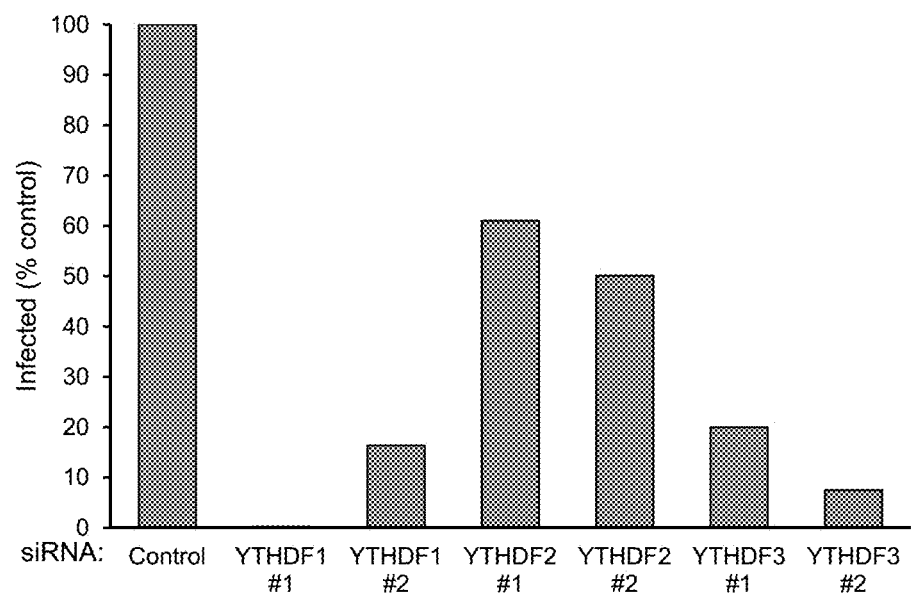
Figure 6:
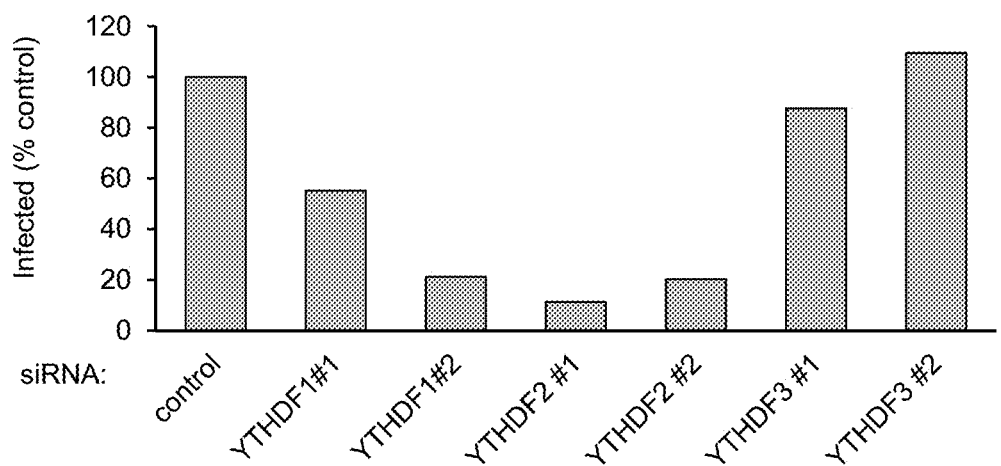

Regulation of Coronavirus Replication and Spread by Cellular m$^6$A Recognition Proteins As discussed above, a family of cellular proteins, termed m$^6$A reader proteins or readers, recognize m$^6$A-modified RNA to influence gene expression post-transcriptionally. Given that m6A installation by METTL3 is necessary for coronavirus replication, we reasoned that recognition of m$^6$A-modified RNA by cellular readers might likewise be required for coronavirus replication. To investigate whether cellular m$^6$A recognition proteins might also regulate coronavirus replication, cytoplasmic host m$^6$A reader proteins YTHDF1, YTHDF2 and YTHDF3 were depleted using RNAi prior to measuring coronavirus reproduction and spread as described in the preceding section. Each reader was depleted using two validated siRNAs and virus replication and spread assayed by indirect immunofluorescence to detect the coronavirus N protein (FIG. 6A). The siRNA agents used are as follows:

```
YTHDF1#1    GUAACGGAGACCAUCAUUU[dT][dT]     (SEQ ID NO: 1)

YTHDF1#2    GUCAAUGGGAGUGGGCAUU[dT][dT]     (SEQ ID NO: 2)

YTHDF2#1    CUGCUUAUCGUUCCAUGAA[dT][dT]     (SEQ ID NO: 3)

YTHDF2#2    GUUCCAUUAAGUAUAAUAU[dT][dT]     (SEQ ID NO: 4)

YTHDF3#1    CAAUUCAAGGGACACUCAA[dT][dT]     (SEQ ID NO: 5)

Mettl3#1    CUGCAAGUAUGUUCACUAUGA[dT][dT    (SEQ ID NO: 6)

Mettl3#2    AGGAGCCAGCCAAGAAAUCAA[dT][dT].  (SEQ ID NO: 7)
```

Depletion of YTHDF1 and YTHDF3, but not of YTHDF2, led to significant reduction in hCoV-OC43 replication and spread in MRCS cells. The reduction in the number of N protein positive cells coincided with a reduction in infectious virus production as measured by TCID$_{50}$ (FIG. 6B). Significantly, depletion of the same readers in Calu-3 cells prior to infection with SARS-CoV-2 revealed a requirement for YTHDF1 and YTHDF2 but not YTHDF3 (FIG. 6C). This demonstrates that coronavirus gene expression and replication is regulated by cellular proteins that recognize m$^6$A-modified RNA. In addition, these results are consistent with and synergize with the demonstration that that coronavirus replication is dependent upon METTL3 catalytic activity.

Example 3

Multiple METTL3 inhibitors derived from different chemical series limit coronavirus reproduction.

Figure 7:
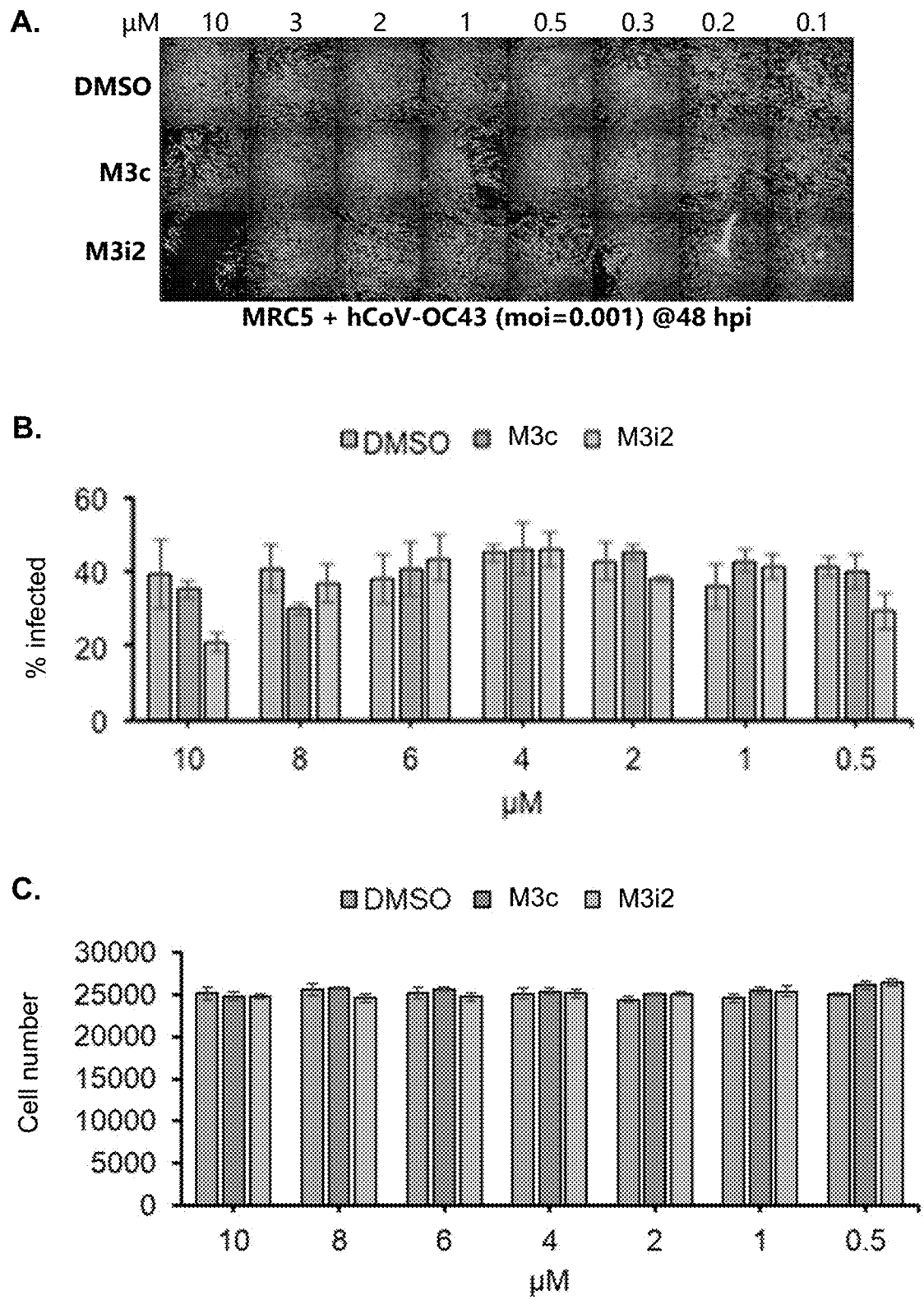
FIG. 7. Chemical inhibition of METTL3 in lung fibroblasts reduces hCOV-OC43 replication. (A) MRCS cells infected with hCOV-OC43 [MOI=0.001] were treated with vehicle (DMSO), control compound (M3c) or active METTL3 inhibitor (M3i2). Viral spread through the culture was determined by immunofluorescence using an antibody to the hCoV-OC43 nucleocapsid protein (green stain). (B) Quantitation of N protein positive cells from (A) (n=3). Suppression of viral replication by M3i2 is evident at 10 mM. (C) Test compounds at the indicated concentrations have no significant impact on MRCS viability (n=3) after 48 h of treatment.
Figure 8:
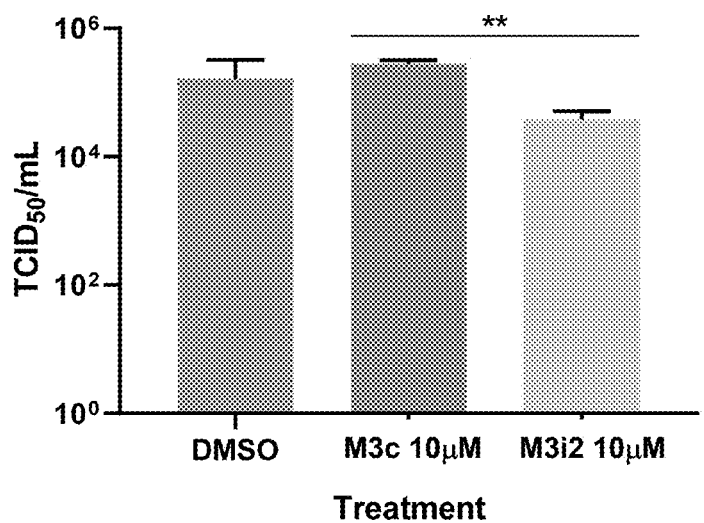
FIG. 8. Inhibiting METTL3 in lung fibroblasts limits hCOV-OC43 infectious virus production. MRCS cells infected with hCOV-OC43 [MOI=0.001] were treated with vehicle (DMSO), control compound (M3c) or active METTL3 inhibitor (M3i2 in A or M3i in B) at the indicated concentration. After 48h, the amount of infectious virus released was quantified by $TCID_{50}$. N=3. **P<0.01; *P<0.05 by student's t-test.
Figure 8:
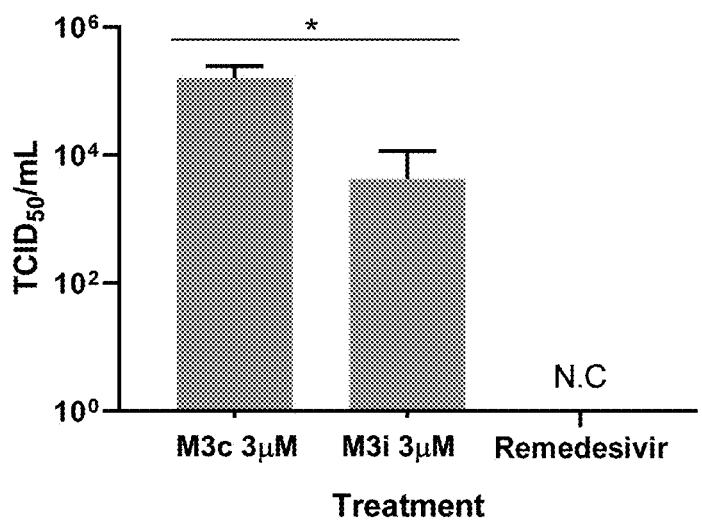

To further demonstrate using METTL3 chemical inhibitors to antagonize coronavirus reproduction, a second METTL3 chemical inhibitor (M3i2) derived from a distinct chemical series was evaluated (FIG. 7A). In FIGS. 7B and 7C, each set of bars from left to right signifies DMSO, M3c and M3i2. Compared to the control compound M3c, 10 μM M3i2 inhibited hCoV-OC43 reproduction and spread through MRCS cells without any discernible effects on cell viability (FIG. 7A-C). To determine how METTL3 chemical inhibitors influenced virus production, we quantified and compared infectious virus produced by infected cell cultures treated with vehicle, a control compound (M3c), the two different METTL3 chemical inhibitors (M3i, M3i2) and remdesivir. Significantly, both M3i and M3i2 reduced hCoV-OC43 infectious virus production compared to equivalent concentrations of M3c or DMSO (FIG. 8A,B). While neither were as efficacious as remdesivir, M3i reduced hCoV-OC43 replication to a greater extent than M3i2 and was active at lower concentrations (FIG. 8. A.B). Thus, two distinct METTL3 inhibitors having different chemical structures and derived from independent chemical series effectively reduced replication of a model human β-coronavirus.

Example 4

The capacity of a METTL3 chemical inhibitor to restrict coronavirus replication requires METTL3.

Figure 9:
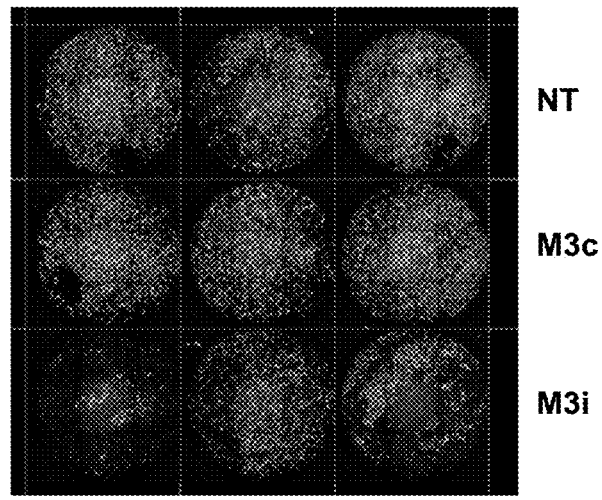
FIG. 9. Inhibition of hCOV-OC43 replication by M3i is dependent upon METTL3. (A) MRCS cells treated with non-silencing siRNA (control) or METTL3-specific siRNA (METTL3-1 or METTL3-2) were infected with hCOV-OC43 [MOI=0.001]. Cultures were either not treated (NT) or treated with a compound unable to inhibit METTL3 (M3c) or active METTL3 inhibitor (M3i). Viral spread through the culture was determined by immunofluorescence using an antibody to the hCoV-OC43 nucleocapsid protein (green stain). (B) Quantitation of N protein positive cells from (A). Note that METTL3-depletion increases N protein positive cells selectively in cultures treated with M3i, but not M3c. (C) Test compounds and siRNAs had at no significant, detectable impact on MRCS viability over the course of the experiment.
Figure 9:
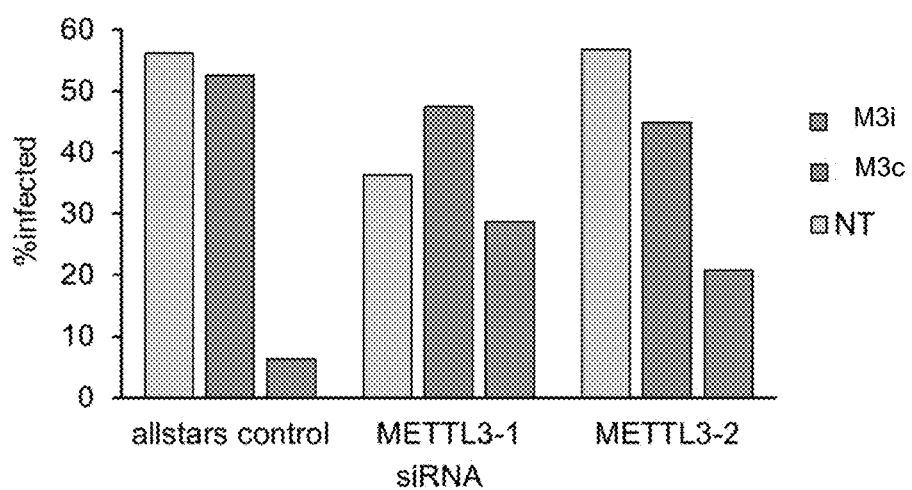
Figure 9:
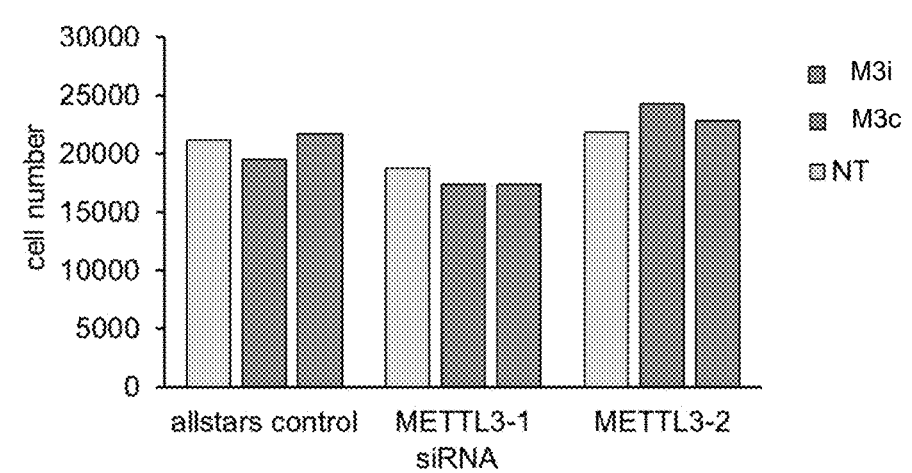

To determine whether the METTL3 chemical inhibitor M3i required the cellular METTL3 gene product to restrict coronavirus replication, MRCS cells were first treated with non-silencing (control) or METTL3 siRNA (either METTL3-1 or METTL3-2). The non-silencing control is from QIAGEN Cat No./ID: 1027281, and has no homology to any currently known mammalian gene. After 48h, cultures were infected with hCoV-OC43 and either untreated or treated with a compound unable to inhibit METTL3 (M3c) or the METTL3 inhibitor M3i. As established in FIG. 2, M3i reduced hCoV-OC43 reproduction and spread in MRCS cells compared to the inactive compound M3c (FIG. 9A,B). The order of the bars in FIGS. 9A and 9B for each set of bars from left to right is non-treated control, M3c, and M3i. While similar levels of virus reproduction and spread were observed in M3c-treated cultures, FIG. 9 shows that METTL3-depletion using either of two distinct siRNAs (METTL3-1, METTL3-2) increased hCoV-OC43 replication and spread specifically in cultures treated with M3i, but not M3c (FIG. 9A,B). Exposure of siRNA-treated cultures to either M3c or M3i did not detectably change cell viability (FIG. 9C). This demonstrates that i) the capacity of M3i to limit coronavirus reproduction and spread is dependent upon METTL3; and ii) depleting METTL3 reduces the inhibitory effect of M3i on hCoV-OC43 replication. Moreover, it is consistent with M3i acting upon or targeting the cellular METTL3 gene product to interfere with the productive replication of human coronaviruses.

Example 5

Figure 10:
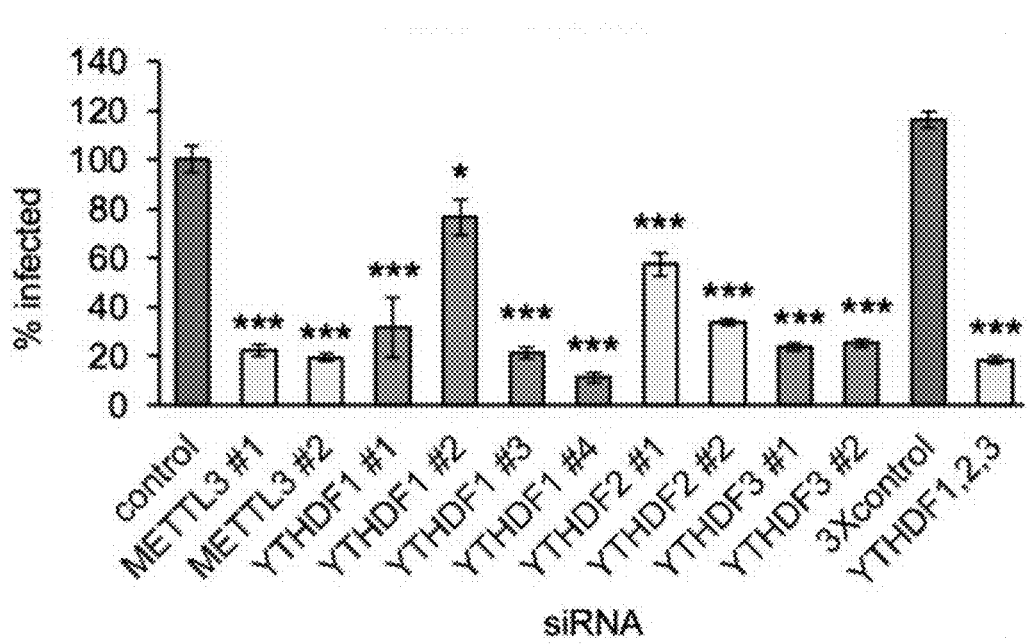
FIG. 10. Focused RNA interference screen implicates METTL3 and the YTHDF readers in control of β-coronavirus replication in A549+ACE2 cells. A549+ACE2 cells were transfected with validated siRNAs targeting METTL3, YTHDF1, YTHDF2, and YTHDF3, either individually or as a mix of single siRNAs to all three YTHDF proteins using siRNA #1 in each case. After 72 h, the cells were infected with icSARS-CoV-2-mNG at MOI=0.1 for 48 h and then fixed and scored for green fluorescence. The extent of spread was normalized to cells transfected with control siRNA. In each case, an ANOVA test with Dunnett multiple comparison correction was used to establish statistical significance compared with control siRNA. (*) P<0.033, () P<0.002, (*) P<0.001.

SARS-CoV-2 Productive Replication in A549+ACE2 Cells is Antagonized by Writer and Reader Depletion We next asked whether the host m6A methyltransferase and m6A recognition proteins also impact the reproduction of the recently emerged pandemic β-coronavirus SARS-CoV-2 by performing a similar RNAi screen in an additional human lung cell infection model-human A549 lung carcinoma cells engineered to constitutively express the human ACE2 receptor (A549+ACE2) (deVries et al. 2021). A SARS-CoV-2 reporter virus expressing mNeonGreen (icSARS-CoV-2-mNG) was used to identify infected cells and directly monitor virus reproduction and spread (Xie et al. 2020). Compared with a control, nonsilencing siRNA, the siRNAs against METTL3 reduced the percentage of infected cells by 78% or 81% (FIG. 10). Likewise, the siRNAs specific for the m6A readers YTHDF2 or YTHDF3 reduced the percentage of mNeonGreen-positive cells by 42%-66% or 75%-76% of the control, respectively (FIG. 10). In contrast, the YTHDF1 siRNAs initially tested reduced SARS-CoV-2 infection to differing degrees: 68% (YTHDF1 siRNA #1) and 23% (YTHDF1 siRNA #2). Testing of two additional YTHDF1-targeting siRNAs (YTHDF1 siRNA #3 and siRNA #4), however, resulted in a 79% and 89% reduction of SARS-CoV-2 compared with control siRNA, consistent with the more robust inhibition observed using YTHDF1 siRNA #1. Codepletion of all three cellular m6A readers reduced the mNeonGreen-positive cell number by 72% (FIG. 10). No major impact on cell viability was detected for any siRNA treatment of A549+ACE2 cells. For this example, the siRNAs included YTHDF1 #3 GAAACGCGGCGUUUGGGCA[dT][dT] (SEQ ID NO:8), and YTHDF1 #4 CACCUACGGACAGCUCAGU[dT][dT] (SEQ ID NO:9). These data further establish that SARS-CoV-2 productive growth is reliant on the major host m6A methyltransferase and cytoplasmic m6A recognition proteins in an additional human lung cell line.

Example 6

Figure 11:
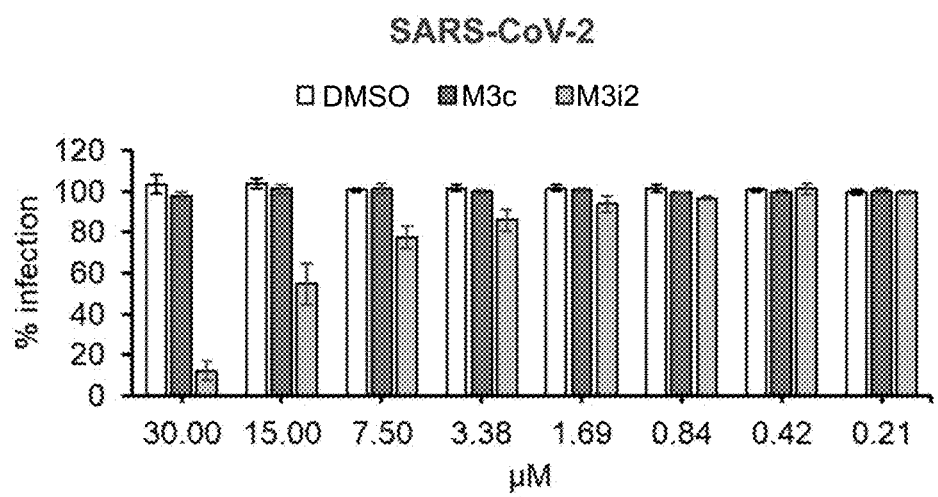
FIG. 11. Inhibition of METTL3 activity suppresses β-coronavirus replication in A549+ACE2 cells. (A) A549+ACE2 cells were infected with icSARS-CoV-2-mNG at MOI=0.1 for 48 h in the presence of METTL3 inhibitor 2 (M3i2, yellow bars), inactive control compound (M3c, gray bars), or vehicle (DMSO, white bars) at the indicated concentrations. The percentage of cells infected was established by green fluorescence and normalized to infection of nontreated cells. (B) The viability of A549+ACE2 cells in the presence of concentrations of each compound used in the infection assays shown in A was assessed using a commercial ATP quantitation assay. Cells were maintained at 37° C. in culture medium containing diluted compound for 48 h prior to lysis. Each experiment was conducted three times with internal duplicates, normalized to DMSO-treated cells processed in parallel and plotted as the mean±SEM. (C) Representative montages showing wells from the infections quantified in A that were treated with 30 μM M3c or M3i2 and infected with icSARS-CoV-2-mNG. (D) Infectious virus titers from A549+ACE2 cells infected with icSARS-CoV-2-mNG at MOI=0.1 and treated with 30 μM either M3c or M3i2 was determined by plaque assay.
Figure 11:
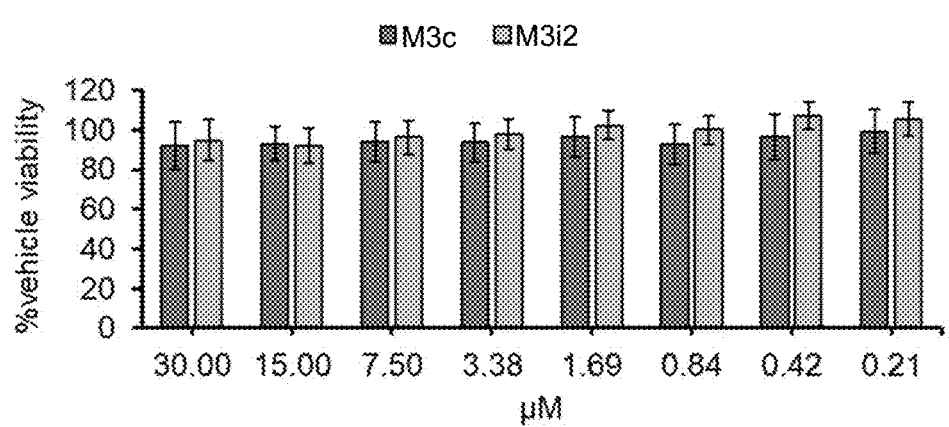
Figure 11:
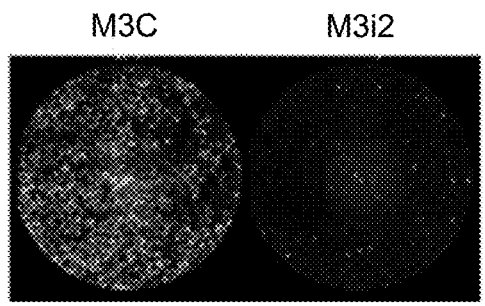
Figure 11:
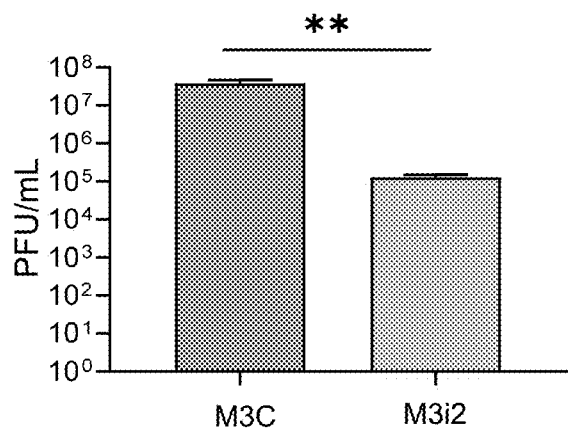

Small Molecule Inhibition of METTL3 Restricts β-Coronavirus Replication and Spread in A549+ACE2 Cells Having established that depletion of either METTL3 or individual cytoplasmic m6A reader proteins interferes with productive replication of SARS-CoV-2 in lung carcinoma A549+ACE2 cells, we asked whether selective inhibition of METTL3 catalytic activity using [M3i2] could also restrict β-coronavirus replication in A549+ACE2 cells. Following low-multiplicity infection of A549+ACE2 cells with SARS-CoV-2, cultures were treated with vehicle (DMSO), the active METTL3 inhibitor (M3i2), or control compound [M3c]. Viral replication and spread was monitored using the high-content imaging platform to score mNeonGreen fluorescence (icSARS-CoV-2-mNG). Compared with DMSO or M3c, the higher concentrations of METTL3 inhibitor M3i2 clearly reduced icSARS-CoV-2-mNG-infected A549+ACE2 cells (FIG. 11A,C). Minor differences in the viability of A549+ACE2 cells were only detected at higher concentrations, indicating that the antiviral activity of M3i2 did not result from general toxicity under these assay conditions (FIG. 11B). SARS-CoV-2 reproduction in A549+ACE2 cells was suppressed by M3i2, with a 10% reduction in mNeonGreen-expressing cells evident at 1.69 µM and increasing in a dose-dependent manner until a >90% reduction at 30 µM (FIG. 11A). The IC50 for M3i2 against SARS-CoV-2 was 16.84 µM.

Quantifying virus replication revealed that M3i2 reduced SARS-CoV-2 infectious virus production in A549+ACE2 cells by 300-fold (FIG. 11D). This concordance further validates the high-content imaging assay as a measure of viral replication and release. Thus, a selective small molecule METTL3 inhibitor effectively suppresses the productive replication of human β-coronavirus, pandemic SARS-CoV-2 in a further human lung cell line.

Materials and methods for examples 5 and 6

Cell Line Data

A549 cells stably expressing human ACE2 [A549+ACE2] (deVries et al 2021) were maintained in DMEM, 10% fetal bovine serum, and penicillin/streptomycin at 37° C. with 5% CO2. Cells were supplemented with puromycin (2 µg/mL) every other passage.

Virus Data

The mNeonGreen expressing SARS-CoV-2 recombinant (icSARS-CoV-2-mNG) based on isolate USA/WA/1/2020 was obtained from the UTMB World Reference Center for Emerging Viruses and Arboviruses.

Cellinsight CX7 LZR High-Content Screening Platform for A549-ACE2 Data

To monitor virus spread in drug treatment and gene knockdown conditions, cells were seeded in black-walled clear-bottom 96-well plates. For icSARS-CoV-2-mNG infection of A549+ACE2 cells, the next day media was removed and replaced with media containing drugs or vehicle control (DMSO) 2 h prior to infection. Cells were infected at MOI=0.1 in the presence of drugs/vehicle and incubated for 48 h at 37° C. Cells were fixed in a 10% formalin solution for 30 min and permeabilized in 0.5% Triton X-100 in PBS for 15 min prior to DAPI staining and a final PBS wash before analysis. Plates were imaged using a CellInsight CX7 LZR high-content screening platform by collecting nine images at 4× magnification to cover the entire well. HCS Navigator software was used to quantify cell number by DAPI staining and the percentage infected cells, indicated by mNeonGreen positivity.

Cell Viability Assay

To determine viability, cells were seeded to opaque white 96-well plates. The next day, cells were drug- or vehicle-treated and incubated as in infection experiments (for example, treated-MRC-5 cells were placed for 48 h at 33° C.). ATP levels were then assayed using Celltiterglo2.0 (Promega G9242) according to the manufacturer's instructions. Luciferase signal was read on a Perkin Elmer Envision 2103 multilabel reader, and 24-h 1 µM staurosporine treatment used as a positive control for assay sensitivity.

This reference listing is not an indication that any reference is material to patentability.

Aguilo F, Zhang F, Sancho A, Fidalgo M, Di Cecilia S, Vashisht A, Lee D F, Chen C H, Rengasamy M, Andino B, et al. 2015. Coordination of m⁶A mRNA methylation and gene transcription by ZFP217 regulates pluri-potency and reprogramming. *Cell Stem Cell* 17: 689-704.

Blanco-Melo D, Nilsson-Payant B E, Liu W C, Møller R, Panis M, Sachs D, Albrecht R A, tenOever B R. 2020. SARS-CoV-2 launches a unique transcriptional signature from in vitro, ex vivo, and in vivo systems. *bioRxiv*. doi: https://doi.org/10.1101/2020.03.24.004655

Burgess H M, Mohr I. 2015. Cellular 5'-3' mRNA exonuclease Xrn1 controls double-stranded RNA accumulation and anti-viral responses. *Cell Host Microbe*. 17: 332-344.

Burgess H M, Mohr I. 2018. Defining the Role of Stress Granules in Innate Immune Suppression by the Herpes Simplex Virus 1 Endoribonuclease VHS. *J Virol*. 92(15). pii: e00829-18.

Channappanavar R, Fehr A R, Zheng J, Wohlford-Lenane C, Abrahante J E, Mack M, Sompallae R, McCray P B Jr, Meyerholz D K, Perlman S. 2019. IFN-I response timing relative to virus replication determines MERS coronavirus infection outcomes. *J Clin Invest*. 130: 3625-3639.

Chen C A, Shyu A B. 2017. Decay Emerging Themes in Regulation of Global mRNA Turnover in cis. *Trends Biochem Sci*. 42: 16-27.

Coots R A, Liu X M, Mao Y, Dong L, Zhou J, Wan J, Zhang X, Qian S B. 2017. m⁶A Facilitates eIF4F-Independent mRNA Translation. *Mol. Cell*. 68: 504-514.e7

Corman, V M, Muth, D, Niemeyer D, Drosten C. 2018. Hosts and sources of endemic human Coronaviruses *Adv. Virus Res*. 100: 163-188.

Courtney D G, Kennedy E M, Dumm R E, Bogerd H P, Tsai K, Heaton N S, Cullen B R. 2017. Epitranscriptomic Enhancement of Influenza A Virus Gene Expression and Replication. *Cell Host & Microbe* 22: 377-386.

Depledge D P, Mohr I, Wilson A C. 2018. Going the Distance: Optimizing RNA-Seq Strategies for Transcriptomic Analysis of Complex Viral Genomes. *J Virol* 93(1). pii: e01342-18.

Depledge D P, Puthankalam S P, Sadaoaka T, Beady D, Mori Y, Placantonakis D, Mohr I, Wilson A C. 2019. Native RNA sequencing on nanopore arrays redefines the transcriptional complexity of a viral pathogen. *Nature comms.* 10(1):754.

Dominissini D, Moshitch-Moshkovitz S, Schwartz S, Salmon-Divon M, Ungar L, Osenberg S, Cesarkas K, Jacob-Hirsch J, Amariglio N, Kupiec M, et al. 2012. Topology of the human and mouse $m^6A$ RNA methylomes revealed by $m^6A$-seq. *Nature* 485: 201-206.

Du H, Zhao Y, He J, Zhang Y, Xi H, Liu M, Ma J, Wu L. 2016. YTHDF2 destabilizes $m^6A$-containing RNA through direct recruitment of the CCR4-NOT deadenylase complex. *Nat. Commun.* 7: 12626.

Edupuganti R R, Geiger S, Lindeboom R G H, Shi H, Hsu P J, Lu Z, Wang S Y, Baltissen M P A, Jansen P W T C, Rossa M, et al. 2017. $N^6$-methyladenosine (m6A) recruits and repels proteins to regulate mRNA homeostasis. *Nat. Struct. Mol. Biol.* 24: 870-878.

Fauci, A S, Lane H C L, Redfield R. 2020. Covid19— Navigating the uncharted. NEJM 382:1268-1269.

Fustin J.-M. et al. 2013. RNA-methylation-dependent RNA processing controls the speed of the circadian clock. *Cell* 155: 793-806.

Garalde D R, Snell E A, Jachimowicz D, Sipos B, Lloyd J H, Bruce M, Pantic N, Admassu T, James P, Warland A, Jordan M, Ciccone J, Serra S, Keenan J, Martin S, McNeill L, Wallace E J, Jayasinghe L, Wright C, Blasco J, Young S, Brocklebank D, Juul S, Clarke J, Heron A J, Turner D J. 2018. Highly parallel direct RNA sequencing on an array of nanopores. *Nat Methods.* 15(3): 201-206.

Geula S, Moshitch-Moshkovitz S, Dominissini D, Mansour A A, Kol N, Salmon-Divon M, et al. Stem cells. m6A mRNA methylation facilitates resolution of naïve pluripotency toward differentiation. Science. American Association for the Advancement of Science; 2015 Feb. 27; 347(6225): 1002-6.

Gokhale N S, McIntyre A B, McFadden M J, Roder A E, Kennedy E M, Gandara J A, et al. 2016. $N^6$-Methyladenosine in Flaviviridae Viral RNA Genomes Regulates Infection. *Cell Host Microbe* 20: 654-665.

Gonzales-van Horn S R, Sarnow P. 2017. Making the Mark: The Role of Adenosine Modifications in the Life Cycle of RNA Viruses. *Cell Host Microbe.* 21: 661-669.

Herdy B, Jaramillo M, Svitkin Y V, Rosenfeld A B, Kobayashi M, Walsh D, Alain T, Sean P, Robichaud N, Topisirovic I, Furic L, Dowling R J O, Sylvestre A, Rong L, Colina R, Costa-Mattioli M, Fritz J H, Olivier M, Brown E, Mohr I, Sonenberg N. 2012, Translational control of the activation of transcription factor NF-κB and production of type I interferon by phosphorylation of the translation factor eIF4E. *Nat Immunol.* 13: 543-550.

Huang C, Lokugarnage K G, Rozovics J M, Narayanan K, Semler B L. Makino S. 2011. SARS coronavirus nsp1 protein induces template-dependent endonucleolytic cleavage of mRNAs: viral mRNAs are resistant to nsp1-induced RNA cleavage. *PLoS Pathog,* 7(12): e1002433.

Haussmann I U, Bodi Z, Sanchez-Moran E, Mongan N P, Archer N, Fray R G, Soller M. 2016. $m^6A$ potentiates Sxl alternative pre-mRNA splicing for robust *Drosophila* sex determination. *Nature.* 540: 301-304.

Jia G, Fu Y, Zhao X, Dai Q, Zheng G, Yang Y, Yi C, Lindahl T, Pan T, Yang Y G, He C. 2011. $N^6$-methyl-adenosine in nuclear RNA is a major substrate of the obesity-associated FTO. *Nat. Chem. Biol.* 7: 885-887.

Ke S, Pandya-Jones, S Y, Fak J J, Vågbø C B, Geula S, Hanna J H, Black D L, Darnell J E Jr, Darnell R B. 2017. $m^6A$ mRNA modifications are deposited in nascent pre-mRNA and are not required for splicing but do specify cytoplasmic turnover. *Genes Dev.* 31: 990-1006.

Kennedy E M, Bogerd H P, Kornepati A V R, Kang D, Ghoshal D, Marshall J B, Poling, B C, Tsai K, Gokhale N S, Horner S M, Cullen B R. 2016. Post-transcriptional m(6)A Editing of HIV-1 mRNAs Enhances Viral Gene Expression. *Cell Host Microbe* 19: 675-685.

Kobayashi M, Arias C, Garabedian A, Palmenberg A C, Mohr I. 2012. Site-specific cleavage of the host poly(A) binding protein by the encephalomyocarditis virus 3C proteinase stimulates viral replication. *J Virol.* 86:10686-94.

Kovaka S, Zimin A V, Pertea G M, Razaghi R, Salzberg S L, Pertea M. 2019. Transcriptome assembly from long-read RNA-seq alignments with StringTie2. *Genome Biol.* 20(1):278.

Leger A, Amaral P P, Pandolfini L, Capitanchik C, Capraro F, Barbieri I, Migliori V, Luscombe N M, Enright A J, Tzelepis K, Ule J, Fitzgerald T, Birney E, Leonardi T, Kouzarides T. 2019. RNA modifications detection by comparative Nanopore direct RNA sequencing. *bioRxiv.* doi: https://doi.org/10.1101/843136

Li Q, Guan X, Wu P, et al. 2020. Early transmission dynamics in Wuhan, China, of novelcoronavirus-infected pneumonia. N Engl J Med. 382:1199-1207. doi: 10.1056/NEJMoa2001316.

Lichinchi G, Gao S, Saletore Y, Gonzalez G M, Bansal V, Wang Y, Mason C E, Rana T M. 2016a. Dynamics of the human and viral m(6)A RNA methylomes during HIV-1 infection of T cells. *Nat. Microbiol.* 1: 16011.

Lichinchi G, Zhao B S, Wu Y, Lu Z, Qin Y, He C, Rana T M. 2016b. Dynamics of Human and Viral RNA Methylation during Zika Virus Infection. *Cell Host Microbe* 20: 666-673.

Linder B, Grozhik A V, Olarerin-George A O, Meydan C, Mason C E, Jaffrey S R. 2015. Single-nucleotide-resolution mapping of m6A and m6Am throughout the transcriptome. *Nat Methods* 12(8):767-72

Liu H, Begik O, Lucas M C, Ramirez J M, Mason C E, Wiener D, Schwartz S, Mattick J S, Smith M A, Novoa E M. 2019. Accurate detection of m6A RNA modifications in native RNA sequences. *Nat Commun.* 9; 10(1):4079.

Liu N, Dai Q, Zheng G, He C, Parisen M, Pan T. 2015. $N^6$-methyl-adenosine-dependent RNA structural switches regulate RNA-protein interactions. *Nature* 518: 560-564.

Liu J, Yue Y, Han D, Wang X, Fu Y, Zhang L, Jia G, Yu M, Lu Z, Deng X, Dai Q, Chen W, He C. 2014. A METTL3-METTL14 complex mediates mammalian nuclear RNA $N^6$-adenosine methylation. *Nat. Chem. Biol.* 10: 93-95.

Liu N, Zhou K I, Parisien M, Dai Q, Diachenko L, Pan T. 2017. $N^6$-methyladenosine alters RNA structure to regulate binding of a low-complexity protein. *Nucleic Acids Res.* 45, 6051-6063.

Lokugamage K G, Narayanan K, Nakagawa K, Terasaki K, Ramirez S I, Tseng C T, Makino S. 2015. Middle East Respiratory Syndrome Coronavirus nsp1 inhibits Host Gene Expression by Selectively Targeting mRNAs Transcribed in the Nucleus while Sparing mRNAs of Cytoplasmic Origin. *J Viol.* 89:10970-81.

Lokugamage K G, Narayanan K. Huang C, Makino S. 2012. Severe acute respiratory syndrome coronavirus protein nsp1 is a novel eukaryotic translation inhibitor that represses multiple steps of translation initiation. *J Virol.* 86: 13598-608, Lokugamage, K G, Schindewolf C, Menachery, V D 2020. SARS-CoV-2 sensitive to type I interferon pretreatment. *bioRxiv* preprint doi: https://doi.org/10.1101/2020.03.07.982264.

Mauer J, Luo X, Blanjoie A, Jiao X, Grozhik A V, Patil D P, Linder B, Pickering B F, Vasseur J J, Chen Q, Gross S S, Elemento O, Debart F, Kiledjian M, Jaffrey S R. 2017. Reversible methylation of $m^6Am$ in the 5′cap controls mRNA stability. *Nature* 541: 371-375. McKinney C, Zavadil J, Bianco C, Shiflett L, Brown S, Mohr I. 2014. Global reprogramming of the cellular translational landscape facilitates cytomegalovirus replication. *Cell Rep.* 6(1): 9-17.

Mer Merkestein M, Laber S, McMurray F, Andrew D, Sachse G, Sanderson J, Li M, Usher S, Sellayah D, Ashcroft F M, Cox R D. 2015. FTO influences adipogenesis by regulating mitotic clonal expansion. *Nat. Commun.* 6: 6792.

Meyer K D, Patil D P, Zhou J, Zinoviev A, Skabkin M A, Elemento O, Pestova T V, Qian S B, Jaffrey S R. 2015. 5′ UTR $m^6A$ promotes cap-independent translation. *Cell* 163: 999-1010.

Meyer K D, Saletore Y, Zumbo P, Elemento O, Mason C E, Jaffrey S R. 2012. Comprehensive analysis of mRNA methylation reveals enrichment in 3′ UTRs and near stop codons. *Cell* 149: 1635-1646.

McIntyre A B R, Gokhale N S, Cerchietti L, Jaffrey S R, Horner S M, Mason C E. 2019. Limits in the detection of m6A changes using MeRIP/m6A-seq. *BioRxiv.* doi: https://doi.org/10.1101/657130

Parker M T, Knop K, Sherwood A V, Schurch N J, Mackinnon K, Gould P D, Hall A J, Barton G J, Simpson G G. 2020. Nanopore direct RNA sequencing maps the complexity of *Arabidopsis* mRNA processing and m6A modification. *Elife.* 14; 9. pii: e49658.

Patil D P, Pickering B F, Jaffrey S R. 2018. Reading $m^6A$ in the Transcriptome: $m^6A$-Binding Proteins. *Trends Cell Biol.* 28: 113-127.

Price A M, Hayer K E, McIntyre A B R, Gokhale N S, Della Fera A N, Mason C E, Horner S M, Wilson A C, Depledge D P, Weitzman M D. 2019. Direct RNA sequencing reveals m6A modifications on adenovirus RNA are necessary for efficient splicing. *BioRxiv.* doi: https://doi.org/10.1101/865485

Roost C. et al. 2015. Structure and thermodynamics of $N^6$-methyladenosine in RNA: a spring-loaded base modification. I *Am. Chem. Soc.* 137: 2107-2115.

Rosa-Mercado N A, Withers J B, Steitz J A. 2017. Settling the $m^6A$ debate: methylation of mature mRNA is not dynamic but accelerates turnover. *Genes Dev.* 31: 957-958.

Roundtree I A, Evans M E, Pan T, He C. 2017. Dynamic RNA Modifications in Gene Expression Regulation. *Cell* 169: 1187-1200.

Rubio R M, Depledge D P, Bianco C, Thompson L, Mohr I. 2018. RNA $m^6A$ modification enzymes shape innate responses to DNA by regulating interferon β. *Genes Dev.* 32: 1472-1484.

Schwartz S, Mumbach M R, Jovanovic M, Wang T, Maciag K, Bushkin G G, Mertins P, Ter-Ovanesyan D, Habib N, Cacchiarelli D, Sanjana N E, Freinkman E, Pacold M E, Satija R, Mikkelsen T S, Hacohen N, Zhang F, Can S A, Lander E S, Regev A. 2018. Perturbation of m6A writers reveals two distinct classes of mRNA methylation at internal and 5′ sites. *Cell Rep.* 8(1): 284-96.

Tirumuru N, Zhao B S, Lu W, Lu Z, He C, Wu L. 2016. N(6)-methyl-adenosine of HIV-1 RNA regulates viral infection and HIV-1 Gag protein expression. *eLife* 5: e15528.

Tzelepis K, de braekeleer E, Yankova E, Rak J, Aspris D, Domingues A F, et al. Pharmacological Inhibition of the RNA m6a Writer METTL3 As a Novel Therapeutic Strategy for Acute Myeloid Leukemia. Blood [Internet]. 2019 Nov. 13; 134 (Supplement_1):403-3. Retrieved from: https://doi.org/10.1182/blood-2019-127962

Vu L P, Pickering B F, Cheng Y, Zaccara S, Nguyen D, Minuesa G, Chou T, Chow A, Saletore Y, MacKay M, et al. 2017. The $N^6$-methyladenosine ($m^6A$)-forming enzyme METTL3 controls myeloid differentiation of normal hematopoietic and leukemia cells. *Nat. Med.* 23: 1369-1376.

Wen J, Lv R, Ma H, Shen H, He C, Wang J, Jiao F, Liu H, Yang P, Tan L, et al., 2018. Zc3h13 Regulates Nuclear RNA $m^6A$ Methylation and Mouse Embryonic Stem Cell Self-Renewal. *Mol. Cell.* 69: 1028-1038.

Winkler R, Gillis E, Lasman L, Safra M, Geula S, Soyris C, Nachshon A, Tai-Schmiedel J, Friedman N, Le-Trilling V T K, Trilling M, Mandelboim M, Hanna J H, Schwartz S, Stern-Ginossar N. 2019. m6A modification controls the innate immune response to infection by targeting type I interferons. *Nat. Immunol.* 20:173-182.

Wu, F., Zhao, S., Yu, B. et al. 2020. A new coronavirus associated with human respiratory disease in China. *Nature* 579, 265-269.

Wang, C., Horby, P. W., Hayden, F. G. & Gao, G. F. 2020. A novel coronavirus outbreak of global health concern. *The Lancet* 395: 470-473.

Wang X, Lu Z, Gomez A, Hon G C, Yue Y, Han D, Fu Y, Parisien M, Dai Q, Jia G, et al. 2014. $N^6$-methyl-adenosine-dependent regulation of messenger RNA stability. *Nature.* 505: 117-20.

Williams G D, Gokhale N S, Horner S M. 2019. Regulation of Viral Infection by the RNA Modification $N^6$-methyladenosine. *Annu. Rev. Virol. July* 5. doi: 10.1146/annurev-virology-092818-015559. [Epub ahead of print]

Wojtas M N, Pandey R R, Mendel M, Homolka D, Sachidanandam R, Pillai R S. 2017. Regulation of $m^6A$ Transcripts by the 3′→5′ RNA Helicase YTHDC2 Is Essential for a Successful Meiotic Program in the Mammalian Germline. *Mol. Cell.* 68: 374-387.

Yue, Y, Liu, J. He, C. 2015. RNA $N^6$-methyladenosine methylation in post-transcriptional gene expression regulation. *Genes Dev* 29: 1343-55.

Zeng Y, Wang S, Gao S, Soares F, Ahmed M, Guo H, Wang M, Hua J T, Guan J, Moran M F, Tsao M S, He F M. 2018. Refined RIP-seq protocol for epitranscriptome analysis with low input materials. *PLoS Biol.* 16(9): e2006092.

Zheng, G. Q. et al. 2013. ALKBH5 is a mammalian RNA demethylase that impacts RNA metabolism and mouse fertility. *Mol. Cell* 49: 18-29.

Zheng Q, Hou J, Zhou Y, Li Z, Cao X. 2017. The RNA helicase DDX46 inhibits innate immunity by entrapping m6A-demethylated antiviral transcripts in the nucleus. *Nat. Immunol.* 18: 1094-1103.

Zhou J, Wan J, Shu X E, Mao Y, Liu X M, Yuan X, Zhang X, Hess M E, Bruning J C, Qian S B. 2018. $N^6$ Methyl-adenosine Guides mRNA Alternative Translation during Integrated Stress Response. *Mol. Cell* 69: 636-647.

Zhou J, Wan J, Gao X, Zhang X, Jaffrey S R, Qian S B. 2015. Dynamic m(6)A mRNA methylation directs translational control of heat shock response. *Nature.* 526: 591-594

Zhou, P., Yang, X., Wang, X. et al. 2020. A pneumonia outbreak associated with a new coronavirus of probable bat origin. *Nature* 579: 270-273.

REFERENCES FOR EXAMPLES 5 AND 6 de Vries M, Mohamed A S, Prescott R A, Valero-Jimenez A M, Desvignes L, O'Connor R, Steppan C, Devlin J C, Ivanova E, Herrera A, Schinlever A, Loose P, Ruggles K, Koralov S B, Anderson A S, Binder J, Dittmann M. 2021. A comparative analysis of SARS-CoV-2 antivirals characterizes 3CLpro inhibitor PF-00835231 as a potential new treatment for COVID-19. *J Virol.* 95:e01819-20. doi: 10.1128/JVI.01819-20.

Xie X, Muruato A, Lokugamage K G, Narayanan K, Zhang X, Zou J, Liu J, Schindewolf C, Bopp N E, Aguilar P V, Plante K S, Weaver S C, Makino S, LeDuc J W, Menachery V D, Shi P Y. 2020. An Infectious cDNA Clone of SARS-CoV-2. *Cell Host Microbe.* 27:841-848.e3. doi: 10.1016/j.chom.0.2020.04.004.

What is claimed is:

1. A method for prophylaxis or therapy for an RNA virus infection, the method comprising modulating the Type I interferon pathway in RNA virus infected cells of the individual by administering one or more agents to the individual that inhibit function of METTL3, wherein the one or more agents are selected from the group consisting of

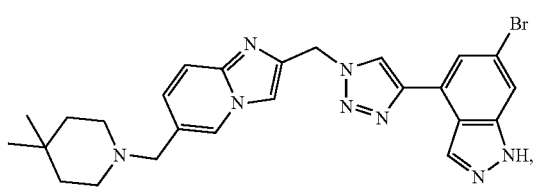

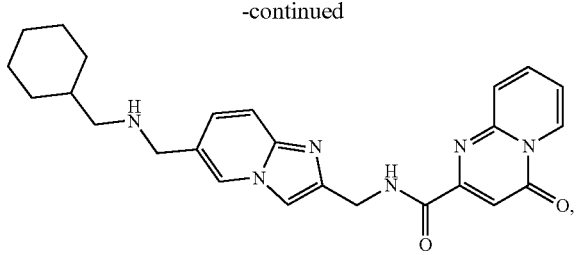

and a combination thereof.

2. The method of claim 1, wherein the individual is infected with a coronavirus.

3. The method of claim 2, wherein the coronavirus is SARS-CoV-2.

4. The method of claim 1, wherein the individual is a human.

5. The method of claim 4, wherein the human has been diagnosed with or is suspected of having COVID-19.

6. The method of claim 1, wherein administering said one or more agents inhibits or prevents transmission of the RNA virus to an individual who is not infected with the RNA virus.

7. The method of claim 4, wherein administering said one or more agents inhibits or prevents transmission of the RNA virus to an individual who is not infected with the RNA virus.

8. A method comprising delivering to RNA virus infected cells one or more agents that inhibit function of METTL3, wherein the one or more agents are selected from the group consisting of:

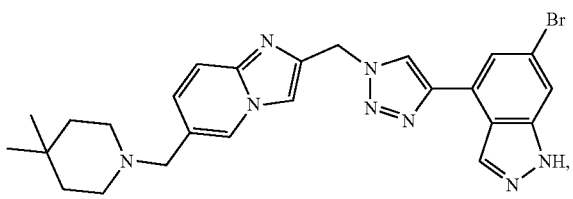

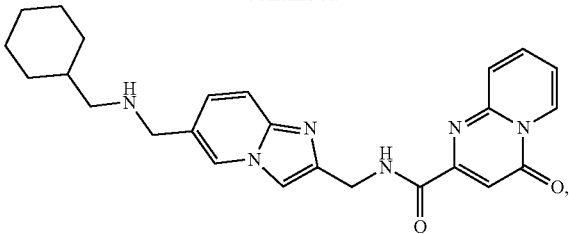

and a combination thereof.

9. The method of claim 8, wherein the RNA virus is a coronavirus.

10. The method of claim 9, wherein the coronavirus is SARS-CoV-2.

* * * * *

UNITED STATES PATENT AND TRADEMARK OFFICE
CERTIFICATE OF CORRECTION

| | | |
|---|---|---|
| PATENT NO. | : 11,944,608 B2 | Page 1 of 1 |
| APPLICATION NO. | : 17/511044 | |
| DATED | : April 2, 2024 | |
| INVENTOR(S) | : Mohr et al. | |

It is certified that error appears in the above-identified patent and that said Letters Patent is hereby corrected as shown below:

In the Specification

Column 1, Line 9 should read:
--STATEMENT REGARDING FEDERALLY SPONSORED RESEARCH OR DEVELOPMENT
This invention was made with government support under AI151358, GM056927, AI073898, and AI152543 awarded by the National Institutes of Health. The government has certain rights in the invention.--

Signed and Sealed this
Fifteenth Day of April, 2025

Coke Morgan Stewart
*Acting Director of the United States Patent and Trademark Office*

SEQUENCE LISTING

```
<160> NUMBER OF SEQ ID NOS: 9

<210> SEQ ID NO 1
<211> LENGTH: 21
<212> TYPE: DNA
<213> ORGANISM: artificial sequence
<220> FEATURE:
<223> OTHER INFORMATION: siRNA

<400> SEQUENCE: 1
guaacggaga ccaucauuut t                                              21

<210> SEQ ID NO 2
<211> LENGTH: 21
<212> TYPE: DNA
<213> ORGANISM: artificial sequence
<220> FEATURE:
<223> OTHER INFORMATION: siRNA

<400> SEQUENCE: 2
gucaauggga gugggcauut t                                              21

<210> SEQ ID NO 3
<211> LENGTH: 21
<212> TYPE: DNA
<213> ORGANISM: artificial sequence
<220> FEATURE:
<223> OTHER INFORMATION: siRNA

<400> SEQUENCE: 3
cugcuuaucg uuccaugaat t                                              21

<210> SEQ ID NO 4
<211> LENGTH: 21
<212> TYPE: DNA
<213> ORGANISM: artificial sequence
<220> FEATURE:
<223> OTHER INFORMATION: siRNA

<400> SEQUENCE: 4
guuccauuaa guauaauaut t                                              21

<210> SEQ ID NO 5
<211> LENGTH: 21
<212> TYPE: DNA
<213> ORGANISM: artificial sequence
<220> FEATURE:
<223> OTHER INFORMATION: siRNA

<400> SEQUENCE: 5
caauucaagg gacacucaat t                                              21
```

```
<210> SEQ ID NO 6
<211> LENGTH: 23
<212> TYPE: DNA
<213> ORGANISM: artificial sequence
<220> FEATURE:
<223> OTHER INFORMATION: siRNA

<400> SEQUENCE: 6
cugcaaguau guucacuaug att                                               23

<210> SEQ ID NO 7
<211> LENGTH: 23
<212> TYPE: DNA
<213> ORGANISM: artificial sequence
<220> FEATURE:
<223> OTHER INFORMATION: siRNA

<400> SEQUENCE: 7
aggagccagc caagaaauca att                                               23

<210> SEQ ID NO 8
<211> LENGTH: 21
<212> TYPE: DNA
<213> ORGANISM: artificial sequence
<220> FEATURE:
<223> OTHER INFORMATION: siRNA

<400> SEQUENCE: 8
gaaacgcggc guuugggcat t                                                 21

<210> SEQ ID NO 9
<211> LENGTH: 21
<212> TYPE: DNA
<213> ORGANISM: artificial sequence
<220> FEATURE:
<223> OTHER INFORMATION: siRNA

<400> SEQUENCE: 9
caccuacgga cagcucagut t                                                 21
```